United States Patent [19]
Goto et al.

[11] 4,410,615
[45] Oct. 18, 1983

[54] LAYERED ELECTROPHOTOGRAPHIC PHOTOSENSITIVE ELEMENT HAVING HYDRAZONE CHARGE TRANSPORT LAYER

[75] Inventors: Satoshi Goto; Akira Kinoshita; Tsuneo Wada, all of Hino; Yoshiaki Takei, Hachioji; Naoko Akashi, Hachioji; Hiroyuki Nomori, Hachioji, all of Japan

[73] Assignee: Konishiroku Photo Industry Co., Ltd., Tokyo, Japan

[21] Appl. No.: 307,087

[22] Filed: Sep. 30, 1981

[30] Foreign Application Priority Data

Oct. 23, 1980 [JP] Japan ................ 55-147544

[51] Int. Cl.³ .......................... G03G 5/14
[52] U.S. Cl. ........................ 430/59; 430/71; 430/900
[58] Field of Search ............ 430/57, 58, 59; 430/900

[56] References Cited

U.S. PATENT DOCUMENTS

| | | | |
|---|---|---|---|
| 3,717,462 | 2/1973 | Negishi et al. | 430/70 |
| 3,765,884 | 10/1973 | Shea | 430/78 |
| 4,150,987 | 4/1979 | Anderson | 430/58 |

FOREIGN PATENT DOCUMENTS

| | | |
|---|---|---|
| 1599 | 5/1979 | European Pat. Off. |
| 39-4298 | 6/1964 | Japan ................ 430/59 |

*Primary Examiner*—J. D. Welsh
*Attorney, Agent, or Firm*—Frishauf, Holtz, Goodman & Woodward

[57] ABSTRACT

An electrophotographic photosensitive element having a conductive support provided thereon with a photosensitive layer comprising a carrier-generating phase and a carrier-transporting phase. The carrier-transporting phase comprises a hydrazone compound to improve carrier-transporting ability having the formula

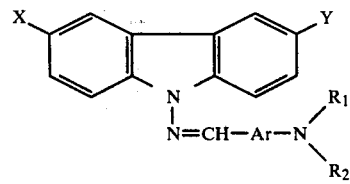

wherein, X and Y each represent a hydrogen or a halogen, $R_1$ and $R_2$ each represent an aryl group which may have a substituent or substituents, and Ar represents an arylene group which may have a substituent or substituents.

26 Claims, 9 Drawing Figures

LAYERED ELECTROPHOTOGRAPHIC PHOTOSENSITIVE ELEMENT HAVING HYDRAZONE CHARGE TRANSPORT LAYER

BACKGROUND OF THE INVENTION

1. Field of the Invention

The present invention relates to an electrophotographic photosensitive element having on a conductive support thereof a photosensitive layer composed in combination of a carrier-generating phase with a carrier-transporting phase.

2. Description of the Prior Art

There have been widely known electrophotographic photosensitive elements which have a photosensitive layer comprised principally of such inorganic photoconductive materials as selenium, zinc oxide, cadmium sulfide and the like. However, these elements cannot necessarily be satisfactory in respect of the stability to heat and durability, and besides have problems in the handling and the manufacture due to their toxic character.

On the other hand, electrophotographic photosensitive elements having a photosensitive layer comprised principally of organic photoconductive compounds have in recent years focused the spotlight of attention upon such various advantages thereof as the relative ease of manufacture, inexpensiveness, ease of handling and the like, and in addition they are generally superior in the stability to heat to those having selenium as the sensitive element thereof. Among such organic photoconductive compounds, poly-N-vinyl carbazole is best known. There has already been made practical reality an electrophotographic photosensitive element having a photosensitive layer comprised mainly of a charge-transfer complex formed from said poly-N-vinyl carbazole and a Lewis acid such as 2,4,7-trinitro-9-fluorenone, while there has been known an electrophotographic photosensitive element having a function-separated photosensitive layer of either the multilayered type or dispersed type constituted so that carrier-generating function and carrier-transporting function may be performed in different material phases respectively; for example, an electrophotographic photosensitive element having a photosensitive layer composed in combination of a carrier-generating layer of amorphous selenium thin layer with a carrier-transporting layer of poly-N-vinyl carbazole is now available for practical use.

However, a layer comprising poly-N-vinyl carbazole has so little flexibility that said layer is hard and fragile, tending to cause cracks and peeling off of the layer, thereby causing the photosensitive element to become less durable, while when a plasticizer is added to improve such defects, the residual electric potential at the time when provided in the electrophotographic process becomes high, and as the element is repeatedly used, the residual electric potential becomes accumulated, thereby gradually producing fog on the reproduced image.

In addition, low molecular weight organic photoconductive compounds are desirable in that they, for lack of film formability, are generally used in combination with a binder, so that, by selecting the kind and composition ratio of binders to be used, the physical or electrophotographic characteristics thereof may be controlled to some extent. However, the number of kinds of organic photoconductive compounds having high compatibility with binders is limited as understood from the fact that only a few are applied to the composition of photosensitive layers for electrophotographic photosensitive element.

For example, the 2,5-bis(p-diethylaminophenyl)-1,3,4-oxadiazole as described in U.S. Pat. No. 3,189,447 has low compatibility with binder that is in general suitably used as materials for the photosensitive layer of an electrophotographic photosensitive element, so that when the material is used to form a photosensitive layer by mixing with such a binder as polyester, polycarbonate in the proportion required for obtaining desirable electrophotographic characteristics, crystals of the oxadiazole come to deposit at a temperature of above 50° C., thereby resulting in the deterioration of electrophotographic characteristics such as the charge acceptance, photosensitivity, etc., while the diaryl alkane derivatives described in U.S. Pat. No. 3,820,989 have no problems in respect of the compatibility with binders, but have little stability to light, so that when applied to the composition of the photosensitive layer of an electrophotographic photosensitive element intended for use in the repetitive transfer type electrophotographic process in which charging-exposure cycle is repeatedly effected, the photosensitivity of the photosensitive layer becomes gradually lowered.

The p-diethylaminobenzaldehyde-diphenylene hydrazone described in Japanese Patent Open to Public Inspection (hereinafter referred to as Japanese Patent O.P.I. Publication) No. 81847/1979 has good compatibility with binder and enables to provide an electrophotographic photosensitive element having relatively good initial characteristics, but said photosensitive element is lacking in durability because as it is repeatedly used, its characteristics such as the sensitivity and the residual potential show a change, and in the concrete the sensitivity becomes gradually lowered and the residual potential becomes accumulated.

As has been mentioned, it is the fact that there are still not found any organic photoconductive compounds having practically suitable characteristics for an electrophotographic photosensitive element.

SUMMARY OF THE INVENTION

It is an object of the present invention to provide an electrophotographic photosensitive element having a carrier-transporting phase composed of organic photoconductive compounds excellent in compatibility with binder, stable to heat and light, and excellent in carrier transporting ability.

It is another object of the present invention to provide an electrophotographic photosensitive element having a photosensitive layer with a high layer strength and excellent in the stability even when repeatedly used.

It is still another object of the present invention to provide an electrophotographic photosensitive element having a high photosensitivity and small residual electric potential.

It is a further object of the present invention to provide a highly durable electrophotographic photosensitive element which, when used as a repetitive transfer type electrophotographic photosensitive element with which a charging-exposure-development-transfer cycle is repeated, is hardly deteriorated with exhaustion after repetitious use and retains stable characteristics for an extended period of time.

As a result of our study to attain the above objects, we have found that the use of specific hydrazone compounds as carrier-transporting materials enables to attain the objects, and thus we have accomplished the present invention.

The foregoing objects are attainable by providing a conductive support thereon with a photosensitive layer comprised in combination of a carrier-generating phase with a carrier-transporting phase comprising a hydrazone compound having formula [A]

(wherein, X and Y each represent a hydrogen or a halogen, $R_1$ and $R_2$ each represent an aryl group which may have a substituent or substituents, and Ar is an arylene group which may have a substituent or substituents.

DETAILED DESCRIPTION OF THE PREFERRED EMBODIMENTS

In the present invention, utilizing the excellent carrier-transporting ability of hydrazone compounds having formula [A], the compound may be used as a carrier-transporting phase component material in the photosensitive layer of the so-called function-separated type photosensitive element wherein the generating and transporting of carrier are carried out separately by different materials respectively, whereby an electrophotographic photosensitive element may be produced which is excellent in respect of the physical properties of the layer and electrophotographic image forming characteristics such as charge acceptance, photosensitivity, residual electric potential and the like, and which is not only hardly deteriorated with exhaustion even when repeatedly used but the said characteristics do not change and is thus capable of displaying stable characteristics.

In the above formula [A], a preferable aryl group is a phenyl group or a substituted phenyl group, and a preferable arylene group is a phenylene group or a naphthylene group. Above groups may have a substituent or substituents which is optional. Preferable substituent is an alkyl group such as a methyl group, an ethyl group, most preferably a lower alkyl group, or a halogen such as chlorine, bromine.

Hydrazone compounds having formula [A] which are useful in the present invention include, for example, those having the following formulas:

Exemplified Compounds

-continued
Exemplified Compounds

(6)

(7)

(8)

(9)

The above-enumerated hydrazone compounds may be readily synthesized in known manners. For example, the N-aminocarbazole and arylaldehyde having the following formulas [B] and [C] respectively are subjected to dehydration-condensation reaction in a solvent such as alcohol in the presence of an acid catalyst, whereby a hydrazone compound having formula [A] is obtained.

Formula [B]　　　　　Formula [C]

Formula [A]

Subsequently, a typical synthesis process of a hydrazone compound applicable to the present invention is illustrated in detail below:

SYNTHESIS EXAMPLE [synthesis of Exemplified Compound (2)]

N-aminocarbazole of 18 g (0.1 mol) and 30 g (0.1 mol) of N,N-ditolylaminobenzaldehyde were dissolved in 500 ml of ethanol, and the solution thus obtained was added with 10 ml of acetic acid and then refluxed by heating for a period of two hours. The deposited crystals thus obtained were filtered, washed thoroughly by ethanol and dried up, whereby Exemplified Compound (2) has been obtained. Yield: 36.4 g, 78.3%, and melting point: 150.0°–151.0° C.

The above-mentioned hydrazone compound may be used not merely in single but in a mixture of two or more kinds thereof, and furthermore in a mixture of one or more kinds thereof with one or more kinds of different carrier-transporting materials, and in the latter case, there is the possibility to form a charge-transfer complex on both the foregoing hydrazone compounds and said different carrier-transporting materials, whereby it may become possible to control arbitrarily the transfer degree of a carrier of a specific sign in said carrier-transporting phase as well as to effectively lose the internal trap. This carrier-transporting phase may at need contain a plasticizer, residual electric potential reducing agent, exhaustion-reducing agent and the like.

Since hydrazone compounds used in the present invention have in themselves no layer formability, the combined use with various binders is required to form a carrier-transporting phase for composing a photosensitive layer.

As binder mentioned herein above, although discretional materials may be used, the most preferaly usable are high molecular polymers capable of forming hydrophobic, highly dielectric and insulating film. Such high molecular polymers may include, for example, compounds enumerated below, but those applicable to the present invention are not limited thereto:
(1) Polycarbonate,
(2) Polyester,
(3) Methacrylic resin,
(4) Acrylic resin,
(5) Polyvinyl chloride,
(6) Polyvinylidene chloride, (7) Polystyrene,
(8) Polyvinyl acetate,
(9) Styrene-butadiene copolymer,
(10) Vinylidene chloride-acrylonitrile copolymer,
(11) Vinyl chloride-vinyl acetate copolymer,
(12) Vinyl chloride-vinyl acetate-maleic anhydride copolymer,
(13) Silicone resin,
(14) Silicone-alkyd resin,
(15) Phenol-formaldehyde resin,
(16) Styrene-alkyd resin,
(17) Poly-N-vinyl carbazole.

These binder materials may be used either in single or in a mixture of two or more kinds.

The afore-mentioned carrier-transporting phase may effectively compose the photosensitive layer of an electrophotographic photosensitive element by the combination thereof with a carrier-generating phase comprised of discretional one selected from among various carrier-generating materials which absorb light to produce carriers.

Suitably usable carrier-producing materials include, for example, those enumerated below:
(1) Selenium, selenium alloys,
(2) Inorganic photoconductive compounds such as CdS, CdSe, CdSSe, HgS,
(3) Perylene dyes such a perylene tetracarboxylic anhydride, perylene tetracarboxylic diimide,
(4) Indigoid pigment,
(5) Polycyclic quinones such as anthraquinones, pyrenequinones, flavanthrones, anthanthrones,
(6) Bisbenzimidazole pigment,
(7) Quinacrydone pigment,
(8) Azo dyes such as monoazo dye, bisazo dye, trisazo dye,
(9) Indanthrone dyes,
(10) Squarylium dyes,
(11) Phthalocyanine pigment such as none-metallic phthalocyanine, metallic phthalocyanine,
(12) Charge-transfer complex formed from electron-donating materials such as poly-N-vinyl carbazole and electron-accepting materials such as trinitrofluorenone, and
(13) Co-crystalline complex formed from pyrilium salt or thiapyrilium salt and polycarbonate.

These carrier-producing materials may be used in single or in combination of two or more, and when making the form of a layer in the case where carrier-generating materials used in single have no film formability, there may be applied thereto one arbitrarily selected from binder materials similar to those used for the carrier-transporting phase.

In the present invention, however, it is particularly preferable to use one selected out of perylene dye, polycyclic quinone, azo dye, or the homologues thereof, as a carrier-generating material.

Figure 1:
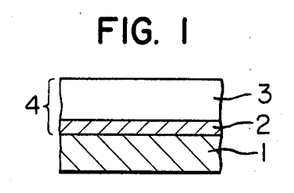
FIGS. 1 through 6 are the respective sectional views of the construction examples of the electrophotographic photosensitive element of the present invention.
Figure 2:
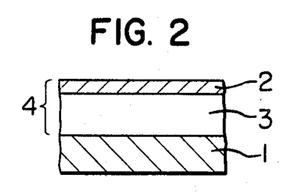
Figure 3:
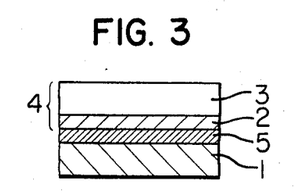
Figure 4:
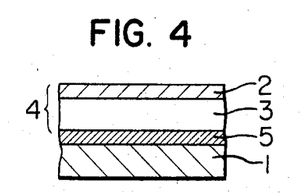
Figure 5:
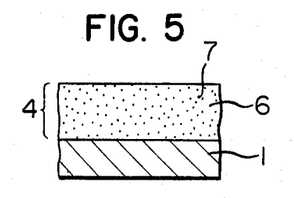
Figure 6:
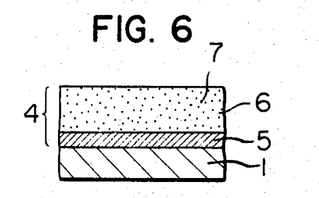

The construction of the electrophotographic photosensitive element of the present invention is illustrated below:

In the present invention, as shown in FIG. 1 and FIG. 2, a conductive support 1 is provided thereon with a photosensitive layer 4 composed of a carrier-generating layer 2 containing as the principal component thereof a carrier-generating material and a carrier-transporting layer 3 containing as the principal component thereof an aforementioned hydrazone compound. As shown in FIG. 3 and FIG. 4, a photosensitive layer 4 may also be provided through an intermediate layer 5 on a conductive support 1. When a photosensitive layer 4 is thus composed of two layers an electrophotographic photosensitive element having excellent electrophotographic characteristics, can be obtained. And in the present invention, as shown in FIG. 5 and FIG. 6, a conductive support 1 may also be provided directly thereon or through intermediate layer 5 with a photosensitive layer 4 composed of a carrier-generating phase 7 prepared by dispersing a carrier-generating material in the powder form into a layer 6 of the carrier-transporting phase containing as the principal component thereof the foregoing carrier-transporting material.

In the case where the photosensitive layer is composed of two layers as described above, which of the carrier-generating layer 2 and carrier-transporting layer 3 should come above depends on the selection of charging polarity; that is, in the case of a negative charge type photosensitive layer, it is advantageous that the carrier-transporting layer 3 comes above because the hydrazone compound in said carrier-transporting layer 3 is a material having a high transportability to positive hole.

The carrier-generating layer 2 of the photosensitive layer 4 which is composed of two layers may be formed directly on either the conductive support 1 or the carrier-transporting layer 3, or at need on an intermediate layer provided such as an adhesive layer, barrier layer, etc., in the manner of
(1) method of vacuum deposition,
(2) method of coating a solution of a carrier-generating material dissolved in an appropriate solvent, or
(3) method of coating a dispersion liquid obtained in the manner that a carrier-generating material is made in the fine particle form in a dispersion medium by means of a ball mill or homomixer and then at need dispersedly mixed with a binder.

The thickness of the thus formed carrier-generating layer 2 is preferably from 0.01 to 5 microns, most preferably from 0.05 to 3 microns, while the thickness of the carrier-transporting layer, though allowed to be changed at need, is preferably normally from 5 to 30 microns.

The proportion of the components composing the carrier-transporting layer 3 is preferably one part by weight of a carrier-transporting material composed principally of the foregoing hydrazone compound to 0.8–4 parts by weight of a binder. However, in the case of forming the photosensitive layer 4 in which a carrier-generating material in the powder form is dispersed, the proportion should preferably by within the range of not more than 5 parts by weight of the binder per part by weight of the carrier-generating material. Further, in the case of composing the carrier-generating layer 2 as of the dispersion type with the use of a binder, the proportion should likewise be within the range of not more than 5 parts by weight of the carrier-generating material per part by weight of the binder.

In addition, as the conductive support 1 for use in composing the electrophotographic photosensitive element there may be used a metallic plate or paper or plastic film provided with conductivity by being coaated, vacuum deposited or laminated with a conductive compound such as, a conductive polymer, an indium oxide or with a thin metallic layer such as, aluminum, palladium, gold. As the intermediate layer 5 such as an adhesive layer, barrier layer there may be used organic polymer such as gelatin, casein, starch, polyvinyl alcohol, vinyl acetate, ethyl cellulose, carboxymethyl cellulose or aluminum as well as high molecular polymers usable as the foregoing binder.

The electrophotographic photosensitive element of the present invention, which is composed as has been described above, as apparent from the hereinafter described examples, is excellent in charging, photosensitivity, and image formability characteristics, and particularly in the durability that it hardly becomes deteriorated with exhaustion even when used in the repetitive type electrophotographic process.

Examples of the present invention are illustrated in detail below, but the embodiment of the present invention is not limited thereto.

EXAMPLE 1

A conductive support made of polyester film laminated with an aluminum foil was provided thereon with an intermediatelayer with the thickness of 0.05 micron made of vinyl chloride-vinyl acetate-maleic anhydride copolymer "S-lec MF-10" (manufactured by Sekisui Chemical Co., Ltd.). On this was vacuum-deposited with dibromoanthanthrone, "Monolite Red 2Y" (C.I. No. 59300-manufactured by I.C.I.), and thus a carrier-generating layer with the thickness of 0.5 micron was formed. Next, two parts by weight of exemplified compound (2) and 3 parts by weight of polycarbonate, "Panlite L-1250" (manufactured by Teijin Chemical Industry Co., Ltd.) were dissolved in 25 parts by weight of 1,2-dichloroethane, and the solution thus obtained was coated so that the layer thickness may become 8 microns after drying to form a carrier-transporting layer, and thus an electrophotographic photosensitive element of the present invention was produced.

The resulting electrophotographic photosensitive element was evaluated on the electrophotographic characteristics thereof in the dynamic system with the use of an electrostatic copying paper Analyser Model SP-428 (manufactured by Kawaguchi Electric Works Co., Ltd.); that is, surface potential $V_A$ when the surface of the photosensitive layer of said photosensitive element was charged for 5 seconds at the charging voltage of $-6.0$ KV; surface potential $V_I$ after being left in the dark for the subsequent 5 seconds; subsequently with a tungsten lamp light controlled so that the illuminance thereof on the surface of the photosensitive element became 35 lux. the exposure (half-decay exposure) $E_{\frac{1}{2}}$ required for reducing surface potential $V_I$ to one second; and surface potential (residual potential) $V_R$ after being exposed with the exposure of 30 lux. sec were found by measurements respectively.

Further, thus obtained electrophotographic photosensitive element was loaded to an electrophotographic copying machine, "U-BiX 2000R" (manufactured by Konishiroku Photo Industry Co., Ltd.) to perform the durability test by repeating 5000 times of a standard process comprising charging-exposure-cleaning steps, and the same measurement was immediately performed again. The results obtained are shown in Table 1.

TABLE 1

|  | After 1st test | After durability test of 5000-time operations |
|---|---|---|
| $V_A$ (V) | −550 | −572 |
| $V_I$ (V) | −456 | −470 |
| $E_{\frac{1}{2}}$ (lux · sec) | 1.8 | 1.8 |
| $V_R$ (V) | 0 | 0 |

As apparent from the above results, a very few fatigue and deterioration and very stable characteristics have been found even after the durability test of 5,000-time operations.

CONTROL EXAMPLES 1-(1)

An electrophotographic photosensitive element for control was prepared in the same manner as in Example 1 with the exception that for the formation of a carrier-transporting layer, benzaldehyde-diphenylene hydrazone was used which have the formula below;

in place of Exemplified Compound (2). The results are shown in Table 2.

TABLE 2

|  | 1st test | After durability test of 5000-time operations |
|---|---|---|
| $V_A$ (V) | −675 | −853 |
| $V_I$ (V) | −522 | −798 |
| $E_{\frac{1}{2}}$ (lux · sec) | 8.4 | 18.2 |
| $V_R$ (V) | −173 | −370 |

As apparent from the above table, the electrophotographic photosensitive element for control was found out to be significantly poor in the characteristics.

CONTROL EXAMPLE 1-(2)

An electrophotographic photosensitive element for control was prepared in the same manner as in Example 1 with the exception that for the formation of a carrier-transporting layer, p-diethylaminobenzaldehyde-diphenylene hydrazone was used which have the formula, in place of Exemplified compound (2).

Figure 7:
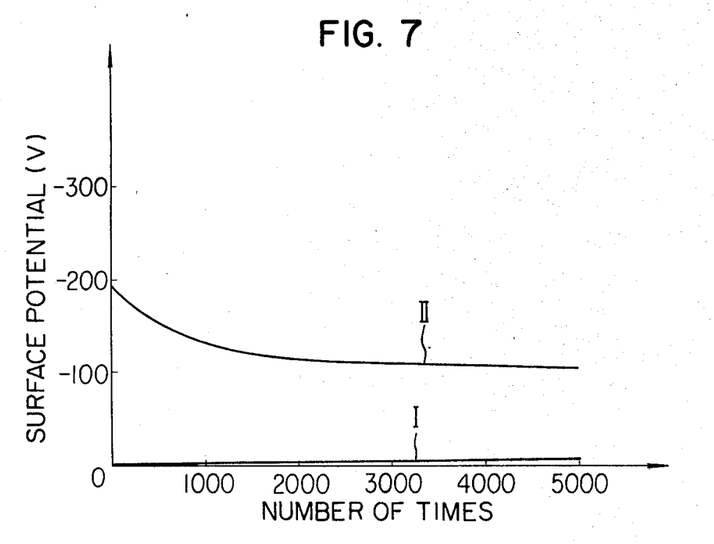
FIG. 7 shows the characteristic curves of an exemplified electrophotographic photosensitive element of the present invention and of a comparison example therewith.

And each sample of the electrophotographic photosensitive element of Example 1 and the electrophotographic photosensitive element of Control Example 1-(2) were loaded respectively in an electrophotographic copying machine, "U-BiX 2000R" (manufactured by Konishiroku Photo Industry Co., Ltd.) to perform the standard process comprising charging-exposure-cleaning steps repeatedly. In order to determine the degree of deterioration from electrical exhaustion (durability) in the processes, each exposure amount of 6 lux.sec was applied to the surface of the photosensitive layer, and how the surface potential of the light-sensitive body obtained at this time changes according to the repetition of the cycle of said processes was examined, then the results as shown in FIG. 7 were obtained wherein curve I is the result of the electrophotographic photosensitive element in Example 1, while curve II shows the result of the control electrophotographic photosensitive element in Control 1-(2). As apparent from these curves the electrophotographic photosensitive element of the present invention is so satisfactory that the change in the surface potential after exposure is small even when repeatedly used, and that the characteristics are stable, whereas the control electrophotographic photosensitive element is low in sensitivity and the surface potential thereof is greatly fluctuated when subjected to a given exposure as the repetition of its use goes on, therefore it has the vital defects to use for a repeating image transfer type photosensitive element for electrophotographic use.

EXAMPLE 2

An electrophotographic photosensitive element of the present invention was produced in the same manner as in Example 1 with the exceptions that a carrier-generating layer was formed by coating a dispersion liquid so that the thickness may become one micron after drying, said dispersion liquid being obtained by adding three parts by weight of bisazo pigment having the formula and one part by weight of polyester, "Polyester Adhesive 49000" (manufactured by Do Pont) into 96 parts by weight of tetrahydrofuran and then by dispersing the mixture thus obtained by means of a ball mill, and that a carrier-transporting layer was formed by coating a coating liquid so that the thickness may become eight microns after drying, said coating liquid being prepared by dissolving two parts by weight of Exemplified Compound (1) and three parts by weight of polycarbonate, "Jupilon S-1000" (manufactured by Mitsubishi Gas Chemicals Co., Ltd.) into 25 parts by weight of 1,2-dichloroethane.

The electrophotographic photosensitive element thus produced was subjected to similar measurements ten times in succession to that of Example 1. The results are shown in Table 3.

TABLE 3

|  | 1st | 10th |
|---|---|---|
| $V_A$ (V) | −735 | −731 |
| $V_I$ (V) | −617 | −613 |
| $E_{\frac{1}{2}}$ (lux · sec) | 5.5 | 5.6 |
| $V_R$ (V) | 0 | 0 |

As apparent from the table, even in the tenth measurements the results show nearly the same stable characteristics as those in the first.

CONTROL EXAMPLE 2

An electrophotographic photosensitive element for control was prepared in the same manner as in Example 2 with the exception that for the formation of a carrier-transporting layer, p-diethylaminobenzaldehyde-diphenylene hydrazone was used which have the formula in place of the exemplified compound (1), and the resulting product was subjected to similar measurements. The results are shown in Table 4.

TABLE 4

|  | 1st | 10th |
|---|---|---|
| $V_A$ (V) | −763 | −825 |
| $V_I$ (V) | −651 | −693 |
| $E_{\frac{1}{2}}$ (lux · sec) | 6.9 | 7.2 |
| $V_R$ (V) | −20 | −35 |

As apparent from the above table, the electrophotographic photosensitive element for control shows significantly deterioration in its characteristics.

EXAMPLE 3

On a conductive support produced by the vacuum deposition of aluminium on a polyester film, a carrier-generating layer was formed by coating the solution so that the amount adhered after drying may be 0.2 g/m², said solution being obtained by dissolving one part by weight of chloro dian blue having the following formula into 140 parts by weight of the mixed solution of ethylene diamine, n-butylamine and tetrahydrofuran of which mixing ratio by weight is 1.2:1.0:2.2 respectively, and then a carrier-transporting layer was formed by coating a coating solution so that the thickness after drying may be 12 microns, said coating solution being obtained by dissolving two parts by weight of Exemplified Compound (3) and three parts by weight of methacrylic resin, "Acrypet" (manufactured by Mitsubishi Rayon Co., Ltd.) into 30 parts by weight of 1,2-dichloroethane, and thus, an electrophotographic photosensitive element of the present invention was produced.

The electrophotographic photosensitive element thus obtained was subjected to measurements similar to those in Example 1, then $E_{\frac{1}{2}}$ was 2.6 (lux.sec) and residual potential $V_R$ was O(V).

The thus produced electrophotographic photosensitive element was subjected to a copying test, using the U-BiX 2000R, then a clearly copied image having a satisfactory contrast and faithful to the original was obtained. Further the same photosensitive element was subjected to a 10,000-time repeated copying test without changing the given exposure, then there were obtained quality image copies as good as the initial one.

EXAMPLE 4

On a conductive support produced by the vacuum deposition of aluminum on a polyester film a carrier-generating layer with the thickness of 0.5 micron was formed by the vacuum deposition of N,N'-dimethyl perylene-3,4,9,10-tetracarboxylic acid diimide "Pariogen Maroon 3920" (C.I. No. 71130, manufactured by BASF). Next, a carrier-transporting layer was formed by coating a liquid so that the thickness becomes 10 microns after drying, said liquid being prepared by dissolving 2 parts by weight of exemplified compound (5) and 3 parts by weight of a polyester "Vylon 200" (manufactured by Toyo Spinning Co., Ltd.) into 30 parts by weight of 1,2-dichloroethane.

The electrophotographic photosensitive element thus obtained was substituted to measurements similar to those in Example 1, then $E_{\frac{1}{2}}$ was 4.3 (lux.sec) and residual potential $V_R$ was O(V).

CONTROL EXAMPLE 3

An electrophotographic photosensitive element for control was produced in the same manner as in Example 4 with the exception that hydrazone compound was used which having the following formula, in place of Exemplified Compound (5), and was subjected to similar measurements, then $E_{\frac{1}{2}}$ was 5.9 (lux.-sec) and $V_R$ was −24(V).

Figure 8:
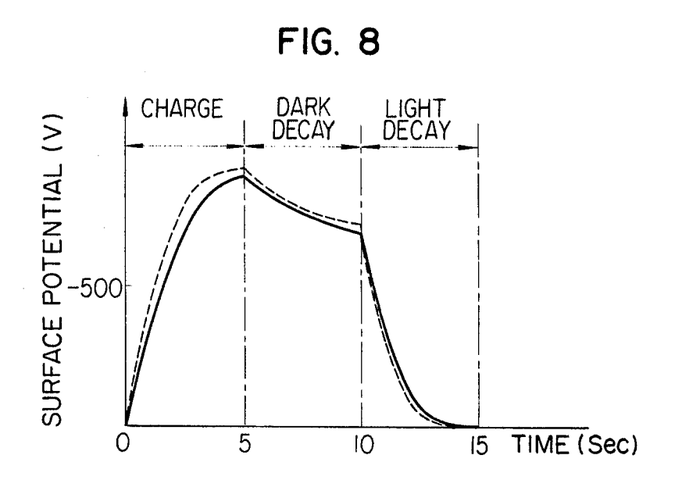
FIGS. 8 and 9 are the respective characteristic of an example of the electrophotographic photosensitive element of the present invention and a control example thereof.
Figure 9:
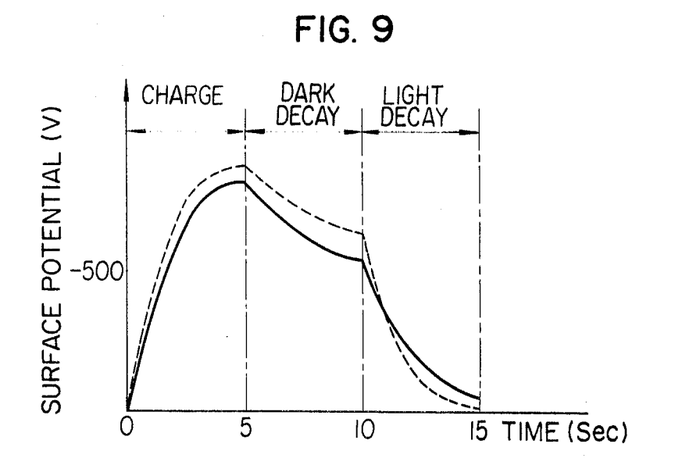

Further, each of the electrophotographic photosensitive element of Example 4 and the electrophotographic photosensitive element for control of Control Example 3 was respectively loaded onto an electrophotographic copying machine, "U-BiX 2000R" to be subjected to 5,000-time repeated charging-exposure-cleaning steps of the standard process for the purpose of a durability test, and when the change on standing was measured in each of the standard process of the first and of the standard process performed after the 5,000-time durability tests had been completed, the respective results have been obtained as shown in FIG. 8 for the electrophotographic photosensitive element of Example 4 and in FIG. 9 for the electrophotographic photosensitive element for control of Control Example 3.

In FIG. 8 and FIG. 9, the dashed lines show the results of the measurements at the first test and the solid lines show the results of the measurements subjected after 5,000-time durability tests. As is obvious from the above results, the electrophotographic photosensitive element of the invention is very excellent in the stability because changes in the respective sensitivity and residual potential are small even after it was used repeatedly.

EXAMPLES 5–8

Electrophotographic photosensitive elements of four kinds in total were produced in the same manner as in Example (1) with the exception that for forming a carrier-transporting layer, Exemplified Compounds (6), (7) and (8) were used respectively in place of Exemplified Compound (2), and were measured the respective $E_{\frac{1}{2}}$ and $V_R$ in the same manner as in Example 1. The results thereof are shown in Table 5.

TABLE 5

| | Hydrazone compounds | $E_{\frac{1}{2}}$ (lux · sec) | $V_R$ (V) |
|---|---|---|---|
| Example 5 | Exemplified compound (6) | 1.9 | 0 |
| Example 6 | Exemplified compound (7) | 2.2 | 0 |
| Example 7 | Exemplified compound (8) | 2.0 | 0 |
| Example 8 | Exemplified compound (9) | 1.9 | 0 |

EXAMPLE 9

On a conductive support produced by the vacuum deposition of aluminium on a polyester film, a carrier-generating layer was formed by coating a dispersed solution so that the thickness coated may become one micron, said dispersed solution being obtained by adding one part by weight of bisazo pigment having the following formula, and one part by weight of polycarbonate, "Panlite L-1250" (manufactured by Teijin Chemicals) into 45 parts by weight of 1,2-dichloroethane and by dispersing the mixture thus obtained by means of a ball mill, and then a carrier-transporting layer was formed by coating a coating solution so that the thickness coated may become 10 microns after dried, said coating solution was prepared by dissolving two parts by weight of Exemplified Compound (1) and three parts by weight of polycarbonate, "Panlite L-1250" into 25 parts by weight of 1,2-dichloroethane, and thus the electrophotographic photosensitive element has been produced.

The electrophotographic photosensitive element thus obtained was subjected to measurements similar to those in Example 1, then $E_{\frac{1}{2}}$ was 5.2 (lux.sec) and $V_R$ was O(V).

What is claimed is:

1. An electrophotographic photosensitive element having a conductive support provided thereon with a photosensitive layer comprising a carrier-generating phase containing a carrier-generating material selected from the group consisting of perylene dyes, polycyclic quinones and azo dyes and a carrier-transporting phase containing a carrier-transporting material wherein said carrier-transporting phase comprises a hydrazone compound represented by the formula wherein, X and Y each represent a hydrogen or a halogen, $R_1$ and $R_2$ each represent an aryl group which may have a substituent or substituents, and Ar represents an arylene group which may have a substituent or substituents.

2. The electrophotographic photosensitive element according to claim 1, wherein said photosensitive layer comprises (i) a layer containing said carrier-generating phase and (ii) a layer containing said carrier-transporting phase.

3. The electrophotographic photosensitive element according to claim 1, wherein said photosensitive layer comprises a carrier-transporting phase-containing layer said carrier-generating phase being dispersed in said carrier-transporting phase-containing layer.

4. The electrophotographic photosensitive element according to claim 1, 2 or 3, wherein said carrier-transporting phase further comprises a binder, said hydrazone compound being dispersed in said binder.

5. The electrophotographic photosensitive element according to claim 1, wherein said aryl group is a phenyl group or a substituted phenyl group.

6. The electrophotographic photosensitive element according to claim 1, wherein said arylene group is a phenylene group or a naphthylene group.

7. The electrophotographic photosensitive element according to claim 1, 2, 3, 5 or 6, wherein said element further comprises an intermediate layer between said conductive support and said photosensitive layer.

8. The electrophotographic photosensitive element according to claim 4, wherein said element further comprises an intermediate layer between said conductive support and said photosensitive layer.

9. The electrophotographic photosensitive element according to claim 1, wherein said substituent is selected from the group consisting of an alkyl group and a halogen.

10. The electrophotographic photosensitive element according to claim 1, wherein said substituent is a lower alkyl group.

11. The electrophotographic photosensitive element according to claim 10, wherein said lower alkyl group is a methyl group or an ethyl group.

12. The electrophotographic photosensitive element according to claim 1, wherein said substituent is a chlorine or a bromine.

13. The electrophotographic photosensitive element according to claim 4, wherein said binder is selected from the group consisting of polycarbonate, polyester, methacrylic resin, acrylic resin, polyvinyl chloride, polyvinylidene chloride, polystyrene, polyvinyl acetate, styrene-butadiene copolymer, vinylidene chloride-acrylonitrile copolymer, vinyl chloride-vinyl acetate copolymer, vinyl chloride-vinyl acetate-maleic anhydride copolymer, silicone resin, silicone-alkyd resin, phenol-formaldehyde resin, styrene-alkyd resin and poly-N-vinyl carbazole.

14. The electrophotographic photosensitive element according to claim 1, wherein said carrier-generating material is selected from the group consisting of perylene dyes, polycyclic quinones, and azo dyes.

15. The electrophotographic photosensitive element according to claim 2, wherein said carrier-transporting phase further comprises a binder, said hydrazone compound being dispersed in said binder, and the ratio of said hydrazone compound and said binder is one part by weight of said hydrazone compound to 0.8-4 parts by weight of said binder.

16. The electrophotographic photosensitive element according to claim 3, wherein said carrier-transporting phase-containing layer further comprises a binder, said hydrazone compound being dispersed in said binder, and the ratio of said carrier-generating material and said binder is not more than 5 parts by weight of said binder per part by weight of said carrier-generating material.

17. The electrophotographic photosensitive element according to claim 2, wherein said layer containing said carrier-generating phase has a thickness of 0.01 to 5 microns and said layer containing said carrier-transporting phase has a thickness of 5 to 30 microns.

18. The electrophotographic photosensitive element of claim 17, wherein said aryl group is a phenyl group or a substituted phenyl group; wherein said arylene group is a phenylene group or a naphthylene group; wherein said carrier-transporting phase comprises a binder having said hydrazone compound dispersed therein; and wherein said layer containing said carrier-generating phase has a thickness of 0.01 to 5 microns and said layer containing said carrier-transporting phase has a thickness of 5 to 30 microns.

19. The electrophotographic photosensitive element of claim 18, wherein said substituents are selected from the group consisting of lower alkyl and halogen.

20. The electrophotographic photosensitive element of claim 18, wherein said substituents are selected from the group consisting of methyl, ethyl, chlorine and bromine.

21. The electrophotographic photosensitive element of claim 20, wherein said carrier-generating material is selected from the group consisting of perylene dyes, polycyclic quinones, and azo dyes.

22. The electrophotographic photosensitive element of claim 21, wherein said binder is selected from the group consisting of polycarbonate, polyester, methacrylic resin, acrylic resin, polyvinyl chloride, polyvinylidene chloride, polystyrene, polyvinyl acetate, styrene-butadiene copolymer, vinylidene chloride-acrylonitrile copolymer, vinyl chloride-vinyl acetate copolymer, vinyl chloride-vinyl acetate-maleic anhydride copolymer, silicone resin, silicone-alkyd resin, phenol-formaldehyde resin, styrene-alkyd resin and poly-N-vinyl carbazole.

23. The electrophotographic photosensitive element of claim 16, wherein said aryl group is a phenyl group or a substituted phenyl group, said arylene group is a phenylene group or a naphthylene group, and wherein said substituents are selected from the group consisting of ethyl, methyl, chlorine and bromine.

24. The electrophotographic photosensitive element of claim 1, wherein said carrier-generating material is dibromoanthanthrone.

25. The electrophotographic photosensitive element of claim 1, wherein said carrier-generating material is an azo dye selected from the group consisting of bisazo pigments of the following formulae (1) and (2) and the chlorodian blue of the formula (3)

26. The electrophotographic photosensitive element of claim 1, wherein said carrier-generating material is the perylene dye N,N'-dimethyl perylene-3,4,9,10-tetracarboxylic acid diimide.

* * * * *